US005733553A

United States Patent [19]

Talwar et al.

[11] Patent Number: 5,733,553
[45] Date of Patent: Mar. 31, 1998

[54] RECOMBINANT BIRTH CONTROL VACCINE

[76] Inventors: Gursaran Prasad Talwar, c/o National Institute of Immunology, Shadid Jeet Singh Marg, New Delhi, India; Jay Srinivasan, Dept. of Biology, Washington University Campus, Box No:1137, One Brookings Dr., St. Louis, Mo. 63130-4899; Sekhar Chakrabarti, c/o The National Institutes of Health, (Room 237, Building 4), Bethesda, Md. 20892

[21] Appl. No.: 263,483

[22] Filed: Jun. 21, 1994

Related U.S. Application Data

[63] Continuation of Ser. No. 844,566, May 27, 1992, abandoned.

[30] Foreign Application Priority Data

Sep. 29, 1989 [CA] Canada ................................ 614520

[51] Int. Cl.⁶ ........................................ A61K 39/00
[52] U.S. Cl. ..................... 424/198.1; 424/199.1; 424/227.1; 435/69.1; 435/69.3
[58] Field of Search ................ 424/198.1, 227.1, 424/199.1; 435/69.1, 69.3

[56] References Cited

U.S. PATENT DOCUMENTS

| 4,738,846 | 4/1988 | Rose et al. | 424/87 |
| 4,780,312 | 10/1988 | Talwar | 424/88 |
| 4,847,080 | 7/1989 | Neurath et al. | 424/89 |

FOREIGN PATENT DOCUMENTS

WO 86/07383  12/1986  WIPO .

OTHER PUBLICATIONS

Talwar et al., "Recent developments in immunocontraception" *American Journal of Obstetrics and Gynecology* (1987) 157:1075–1078.

Lall et al., "Recombinant vaccinia virus express immunoreactive alpha subunit of ovine luteinizing hormone which associates with β–hCG to generate bioactive dimer" *Indian Journal of Biochemistry & Biophysics* (1988) 25:510–514.

Edwards, Rg. Conception in the Human Female, pp. 200–201, 1980, Academic Press.

Niles, E.D., et al., "Vaccinia virus gene D8 encodes a virion transmembrane protein" *J. Viol.* (1988) 62(10):3772–3778.

Chakrabarti, S., et al., "Expression of biologically active human chorionic gonadotropin and its subunits by recombinant vaccinia virus" *Gene* (1989) 77:89–93.

Smith, G.L., et al., "Infectious vaccinia virus recombinants that express hepatitis B virus surface antigen" *Nature* (1983) 302:490–495.

Primary Examiner—Lila Feisee
Assistant Examiner—Julie E. Reeves
Attorney, Agent, or Firm—Morrison &Foerster

[57] ABSTRACT

A recombinant birth control vaccine comprising a beta subunit of chorionic gonadotropin, a recombinant luteinizing hormone or a mixture thereof has been developed. This recombinant birth control vaccine may also act as a vaccine against a protein or peptide unassociated with the mammalian reproductive system, such as a protein or peptide associated with a disease organism such as hepatitis B.

8 Claims, 12 Drawing Sheets

FIG. 5
STRATEGY FOR THE CONSTRUCTION OF
βhCG - HBsAg (Pre S₂ + S)

RECOMBINANT BIRTH CONTROL VACCINE

This application is a continuation of application Ser. No. 07/844,566, filed May 27, 1992 now abandoned.

Population is growing at a rapid pace in many economically developing countries and there is a continuing need of an alternate method for regulation of fertility. We proposed several years back a birth control vaccine which induces the formation of antibodies against the human pregnancy hormone, the human chorionic gonadotropin (hCG). These inventions are described in patents issued in India, U.S.A. and several other countries. (Ref. EP 204566, JP 62286928, CA 1239346, U.S. Pat. No. 4,780,312, CN 8603854). We describe now another invention which generates antibody response of a long duration against hCG after a single or a limited number of injections.

Whereas the possibility of controlling fertility by raising antibodies against hCG is known from our previous studies and those of others, the vaccines utilized earlier were conjugates of two or more peptides such as the natural beta hCG peptide of 145 amino acids linked to tetanus toxoid or other carriers. In another modality, the beta hCG peptide was associated with alpha oLH and then linked to carriers (Talwar et al 1988; U.S. Pat. No. 4,780,312). These vaccines demand purification and preparation of the constituent proteins from natural sources. The cost of some of these is at present very high which will be restrictive to their large scale use in family planning programs of economically developing countries. Moreover these vaccines demand three injections for primary immunization followed by a fourth as booster. A major advantage of the present embodiment is the possibility of getting satisfactory and sustained antibody response with one primary injection and at most one booster. Another interesting feature is the low cost at which this vaccine can be prepared and made available for large scale use.

Vaccinia virus is well known as a versatile tool for molecular biologists. In the New Scientist dated 3 Dec., 1988 (Anon, p.38) an article refers to a new vaccine for rinderpest virus in cattle and states that the vaccine is a genetically engineered version of the vaccinia virus, researchers having transformed two genes coding for the coating of rinderpest virus into the vaccinia virus.

In a Tibtech article dated January 1990, Miner et al (p. 20–25), discusses vaccinia virus as a versatile tool for molecular biologists and suggests that "the vaccinia virus system is a promising way of producing significant amounts of correctly processed and modified eukaryotic proteins in mammalian cells".

U.S. Pat. No. 4,603,112 (inventors: E. Paoletti et al; issued: Jul. 29th, 1986) discloses methods for modifying the genome of vaccinia virus to produce recombinant vaccinia virus comprising DNA not naturally occurring in vaccinia virus. While this reference includes reference to the heterologous DNA coding for a protein which may be an antigen, it does not appear to make any suggestion that this technology is a route to birth control vaccines or birth control vaccines which also double-up as vaccines capable of raising antibodies against proteins or peptides unassociated with the mammalian reproductive system.

PCT publication No. WO88/06626 (inventors: B.R. Bloom et al; filed: 29 Feb., 1988) relates to the use of recombinant mycobacteria as vehicles capable of expressing foreign DNA. It also indicates that such mycobacteria could be used as an anti-fertility vaccine vehicle. However, it appears to make no claim to the use of mycobacteria for control of fertility and also directs readers away from the use of vaccinia in this field pointing out alleged disadvantages on pages 4 and 5.

Therefore there appears to be a need to provide a safe, simple and effective birth control vaccine at low cost which can also, if required, act as a vaccine against non-reproductive-system-associated disorders such as infections by bacteria and viruses. While some of the references suggest the use of vaccinia as a biotechnological tool, other references, especially Bloom et al appear strongly to discourage consideration of vaccinia. In view of the expenses involved in this type of research it therefore cannot be said that there are clear signposts to research works in this area pointing to the use of vaccinia in birth control vaccines.

The present invention therefore provides a nucleotide sequence comprising a first sequence coding for a mammalian reproductive peptide hormone or active fragment thereof or a mammalian reproductive peptide hormone or active fragment thereof in reading frame alignment with a gene or gene fragment coding for a protein or peptide unassociated with a mammalian reproductive system and a second sequence coding for at least part of a vaccinia virus genome.

The invention also provides a nucleotide sequence comprising a first sequence coding for (a) a beta subunit of a chorionic gonadotropin, (b) an alpha subunit of a luteinizing hormone or (c) either a beta subunit of chorionic gonadotropin or an alpha subunit of luteinizing hormone in reading frame alignment with a gene or gene fragment coding for a protein or peptide unassociated with a mammalian reproductive system and a second sequence coding for at least part of a vaccinia virus genome.

The invention also provides a nucleotide sequence comprising a first sequence coding for (a) a beta subunit of human chorionic gonadotropin, (b) an alpha subunit of ovine luteinizing hormone or (c) either a beta subunit of human chorionic gonadotropin or an alpha subunit of ovine luteinizing hormone in reading frame alignment with a gene or gene fragment coding for a hepatitis B surface protein, and a second sequence coding for at least part of a vaccinia virus genome.

The above nucleotide sequences are preferably inserted into a nonessential part of a vaccinia virus genome to give a recombinant vaccinia virus.

The vaccine may consist of the genes of beta subunit of hCG fused at the DNA level with a gene fragment coding for a trans-membrane protein or peptide. A preferred trans-membrane peptide comprises 49 amino acids. A companion vaccine may consist of a physical mixture of vaccinia-beta hCG(e.g. vSS2) and vaccinia-alpha ovine luteinizing hormone(oLH)e.g. (vSL5).

According to the present invention there is provided a birth control vaccine comprising a recombinant beta subunit of human chorionic gonadotropin, a recombinant alpha ovine luteinizing hormone or a mixture thereof.

A preferred embodiment comprises a recombinant virus, e.g. vSS2, in which the gene for the beta subunit of hCG fused with the gene coding for a trans-membrane peptide is inserted in vaccinia virus.

A further preferred embodiment comprises a recombinant virus such as vSL5, in which the gene for the alpha subunit of oLH is inserted in vaccinia virus.

Another preferred embodiment comprises a recombinant virus in which a first nucleotide sequence comprises the beta unit of human chorionic gonadotropin in reading frame alignment with a gene coding for the middle protein of hepatitis B surface protein. Other proteins from other organisms, especially pathogens, or even synthetic sequences can be coded in place of hepatitis B proteins.

BRIEF DESCRIPTION OF THE DRAWINGS

In drawings which illustrate embodiments of the invention;

FIG. 2 shows the strategy for the insertion of alpha oLH gene into vaccinia virus; and, FIG. 3 demonstrates the anti hCG response in terms of antigen binding capacity. The figure shows typical antibody response in four rats given a single injection of vSS2 recombinant vaccine at a dose of 10 pfu (plaque forming units). Each animal response with antibodies in circulation measurable at the end of four weeks. The titers ranged from 100 to 900 ng/ml and are distinctly above the threshold value of 20 ng/ml considered to be protective against pregnancy. The titers were sustained over 12 weeks of observation.

FIGS. 4*a* to 4*h* show development of hCG antibodies in 8 bonnet monkeys injected with vSS2 recombinant vaccine.

FIG. 5 shows the strategy for the construction of BhCG-HBsAg. The final plasmid, pSS4 is shown along with the junction sequences between BhCG and HBsAg.

FIG. 6 shows a southern blot of pSS4. Nick-translated S gene was used as the probe and washed at high stringency.

FIG. 7 shows subcloning of hepatitis B genome in pUC plasmids.

FIG. 8 gives assay results for BhCG and HBsAg. On the X-axis are the three parallel purified recombinants of the virus vSS4 (1,2 and 3) along with vSS2, an internal control and Abbott's positive and negative controls.

FIG. 9 shows development of hCG antibodies in 7 rats injected with vSS4 recombinant vaccine.

EXAMPLE 1

Synthesis and Utility of Recombinant Anti-hcG Vaccine

The construction strategy of vSS2: The virus containing the anchored beta hCG was made by an in-frame fusion of the trans- membrane and cytoplasmic domains of the gene coding for vesicular stomatitis virus glycoprotein (VSVg) to the 3 ' end of the beta hCG cDNA (FIG. 1). The VSVg gene was digested with Alu I and Xho I to release the 249 bp membrane anchor sequence. This fragment was eluted out from an acrylamide gel, klenow filled and ligated to the Sma I cut vector pSS I, the latter was prepared by the procedure described by us previously (Chakrabartit et al 1989). Orientation of the anchor sequence with reference to beta hCG was checked by suitable restriction enzyme digestions. This was used to transfect CV-1 cells pre-infected with wild type virus and the recombinants were picked up by visual screening for the blue plaques by the technique described elsewhere.

Assay for beta hCG

The expression of beta hCG was detected in the pellet of the vSS2 infected cells by a competitive radio-immunoassay using mouse monoclonal antibodies raised against beta hCG. The cellular localisation of hCG was determined by immunofluorescence technique using anti beta hCG MoAb followed by rabbit anti mouse conjugated to FITC.

Immunogenic properties: A single intra-dermal injection of $10^8$ pfu of vSS2 elicited the formation of antibodies in rats which reacted with hCG (FIG. 3) and prevented effectively the binding of hCG to receptors on target tissue. The antibodies were detectable within four weeks. The titers were sustained without a decline over a period of several months.

Antibody titers in monkeys immunized with recombinant anti hCG vaccine (vSS2):

Bonnet monkeys (*Mecacca radiata*) were immunized intradermally with $10^8$ pfu of the recombinant vaccine. Two immunizations were done at 3 months interval (day 0 to 95). Four months later (day 226), a booster injection of 100 ug of beta hCG adsorbed on alum was given intramuscularly. Anti hCG antibodies were measured (□—□) by radio-immunoassay (see Om Singh et al). These are expressed on the ordinate on a logarithmic scale. The antibody titers were measurable after the first immunization with the recombinant vaccine. Their titers after two primary and a booster injection increased to very high levels ranging from 3,200 to 14,000 ng of hCG binding capacity per ml. These antibodies had high affinity (ka= $10^{-11}$LM). The antibodies were competent to prevent the binding of hCG to the target tissue receptors as determined by competitive radio receptor assays (+—+). The competence of the antibodies in neutralizing the bioefficacy of hCG indicates the efficacy of immunization with such vaccines in order to intercept events supported by hCG, such as the establishment and sustenance of early pregnancy.

FIG. 4 gives data in eight monkeys to demonstrate the consistency of the phenomenon. These experiments also demonstrate the immunogenicity of these products not only in rodents but also in primates (and, by extension, humans).

To date, the best results in both monkeys and rats have been obtained with $10^8$ pfu. An operating range runs from about $10^9$ down to about $10^4$ pfu, preferably of the order of $10^7$ to $10^8$ pfu. Interestingly, dose does not appear to work in this case on a body weight basis and this may be related to the use of live vaccine. Attenuation by passaging may be useful to avoid possible side effects.

EXAMPLE 2

Synthesis and Utility of Anti-oLH Vaccine

Construction of vSL5: The alpha oLH cDNA was cut out by the restriction enzyme Bgl II from a previously described vector (Lall et al 1988). This fragment was klenow filled, ligated to 8-mer Eco RI linkers and cloned into the unique Eco RI site of the vaccinia vector pSC45 (FIG. 2). The final plasmid, pSL5, was characterised in detail with respect to the correct orientation of the alpha oLH gene by multiple restriction enzyme digestions and Southern hybridization. This plasmid was subsequently used in DNA transfection to construct the recombinant virus vSL5 as described earlier.

Assay for alpha oLH

The medium of the cells infected with recombinant virus vSL5, was assayed for the presence of alpha oLH by a competitive radio-immunoassay using anti alpha oLH antibodies raised in monkeys. The expression of alpha oLH was quantitated using a standard subunit peptide. The presence of alpha oLH could be detected within three hours of infection and was found to be 280 ng/ml/3×$10^6$ cells in 24 hours.

EXAMPLE 3

Production of Mixed Recombinant Vaccines

Biological activity: The alpha oLH subunit associates with beta hCG to form a hetero-dimer. The ability of this hetero-dimer to stimulate steroidogenesis in a Leydig cell system is well-established (Talwar et al., 1988). In order to show that the recombinant alpha oLH-beta hCG hetero-dimer retains its biological activity, a co-infection of viruses vSS1 and vSL5 was done in the CV1 cells and the supernatant, collected 24h post-infection was used in a Leydig cell bio-assay. The steroidogenesis elicited by the vaccinia expressed alpha oLH-beta hCG hetero-dimer was greater than the native hCG dimer indicating the correct and full length expression of the two peptides.

A similar and somewhat bio-effectively better immune-response to that shown by construct vSS2 alone could be generated by using a mixture of the constructs vSS2 and vSL5. It is known from other studies that the antibodies generated by a heterospecies dimer of beta hCG and alpha oLH have about 25% better bio-efficacy as a function of their immunological titers as compared to those generated to beta hCG alone.

EXAMPLE 4
Production of a Recombinant Birth Control Vaccine Also Having Other Antigenic Properties Associated With The Same Nucleotide Sequence The gene for beta hCG together with sequences enabling it to anchor on the membrane of the infected cells is one effective modality to induce antibodies against hCG.

Another modality which results in production of hCG antibodies together with protection against hepatitis B viral infection is as follows:

The gene for beta hCG is cloned in right alignment and in-frame with the gene coding for hepatitis B surface protein, which includes the portion coding for the S region of the protein as well as the pre S2 region. The manner in which this construct is prepared is exemplified below.

Figure 1:
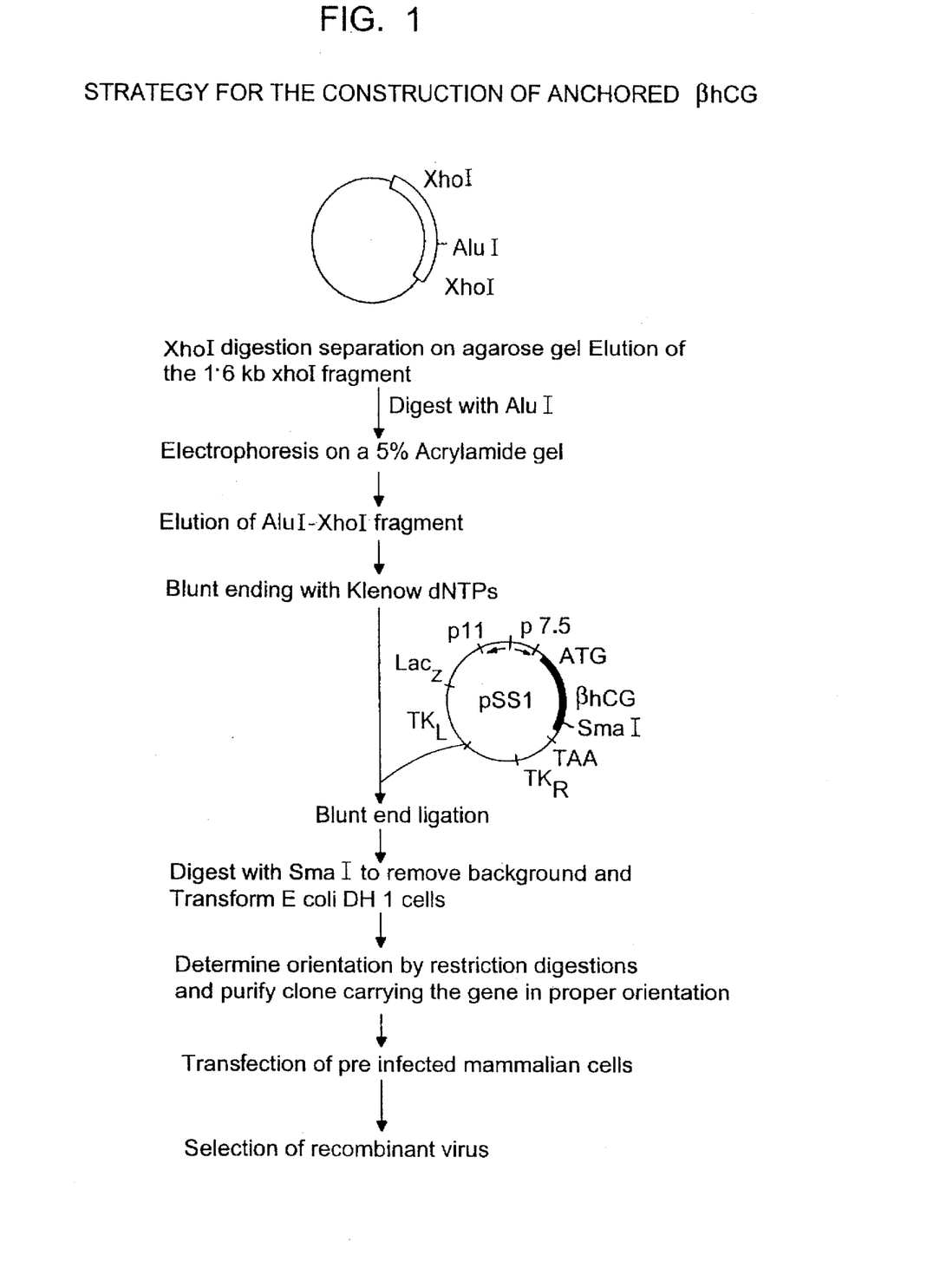
FIG. 1 shows the strategy for the construction of anchored beta hCG.
Figure 2:
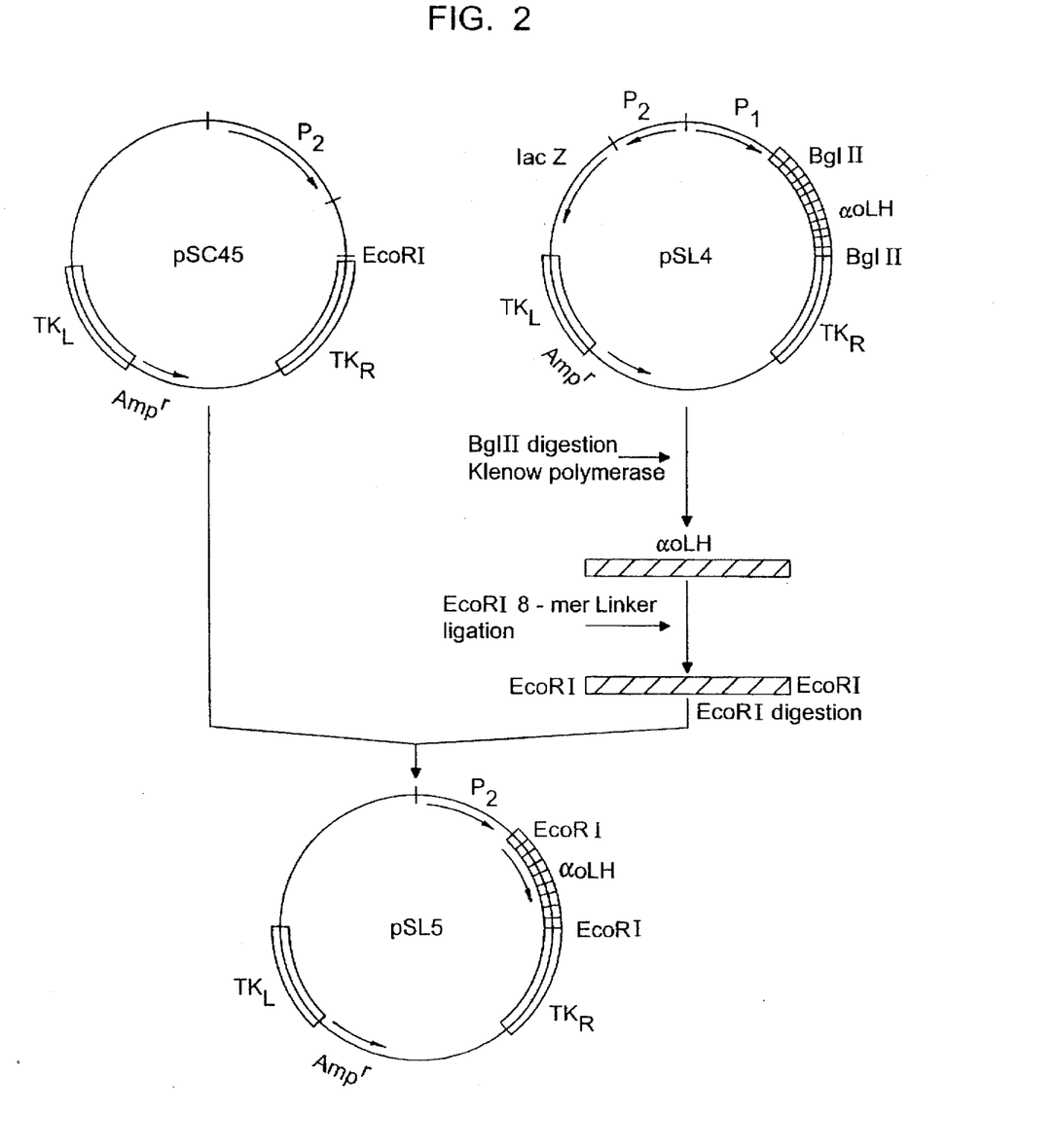
Figure 3:
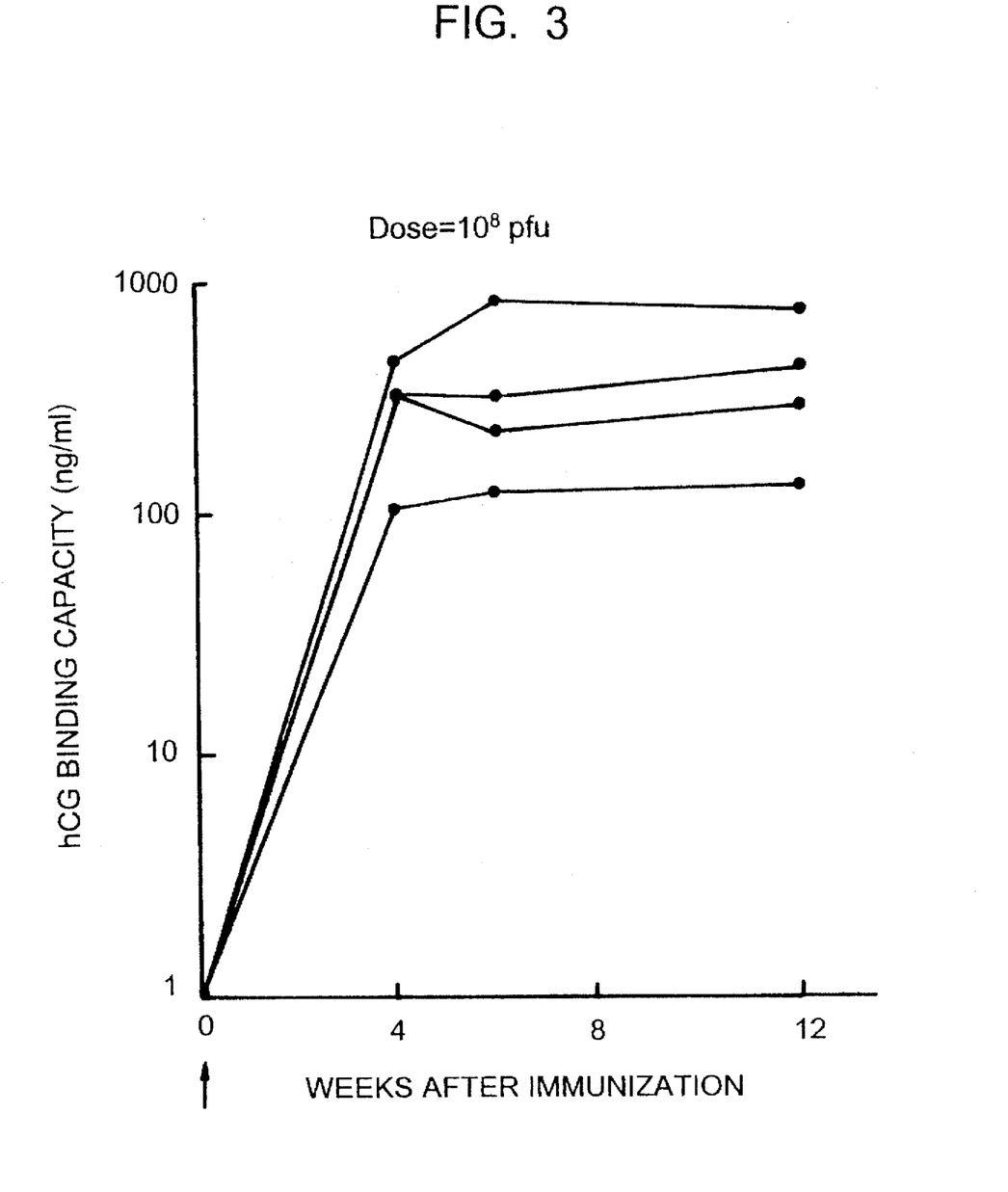
Figure 4A:
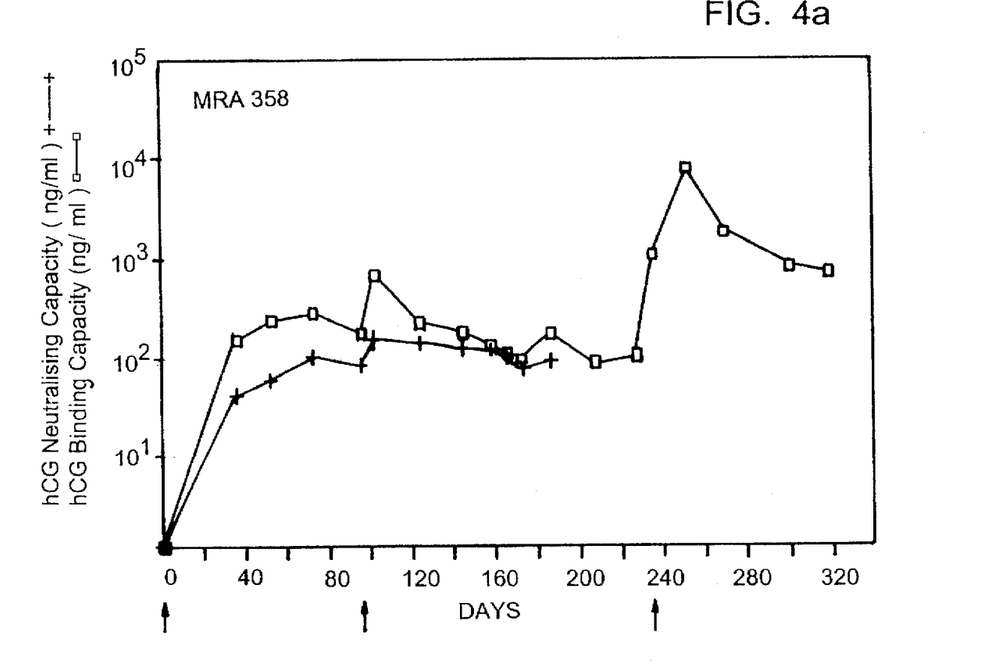
Figure 4B:
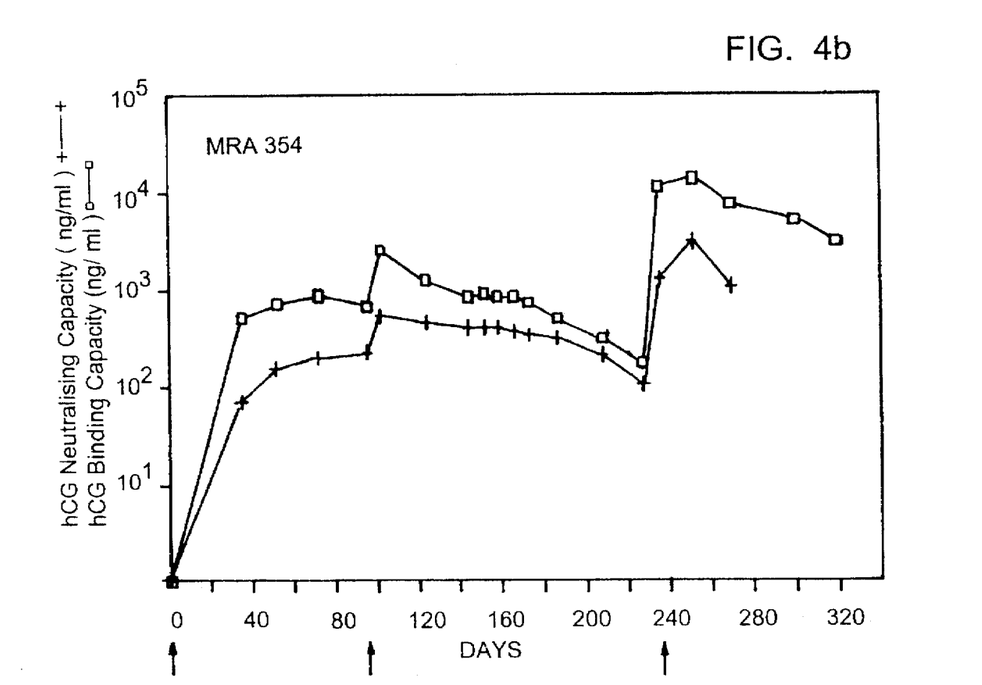
Figure 4C:
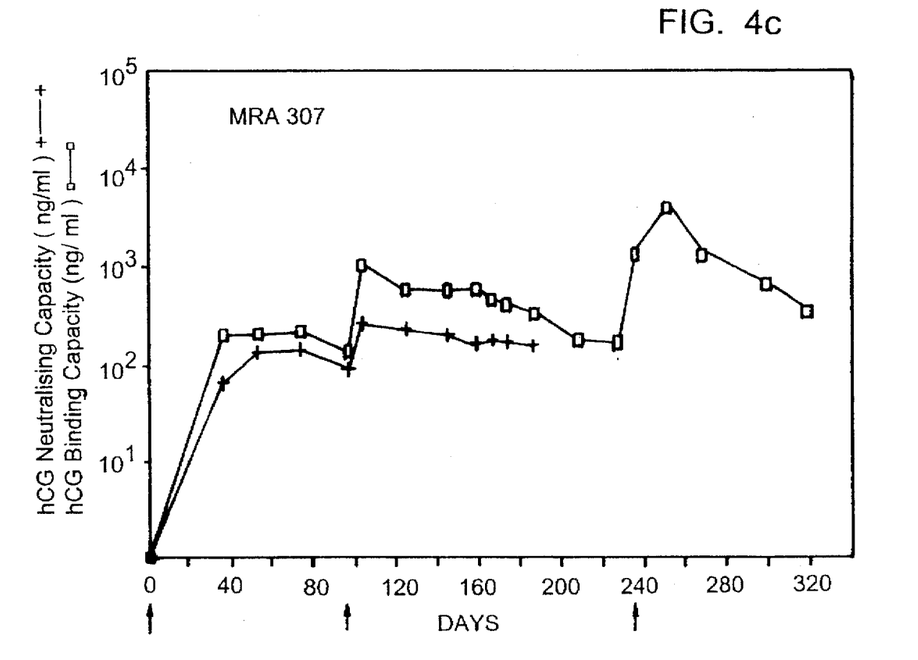
Figure 4D:
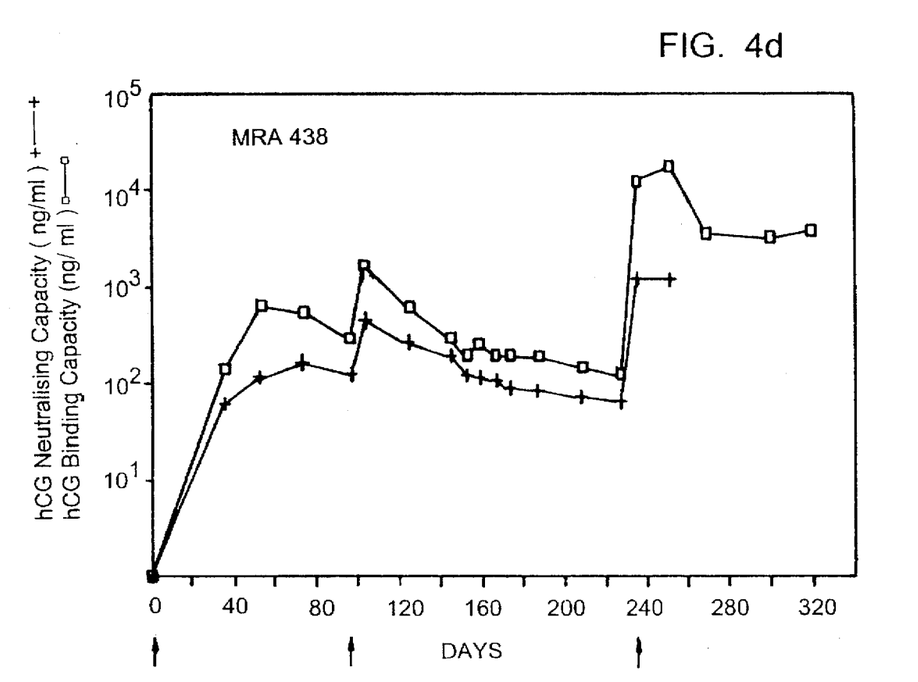
Figure 4E:
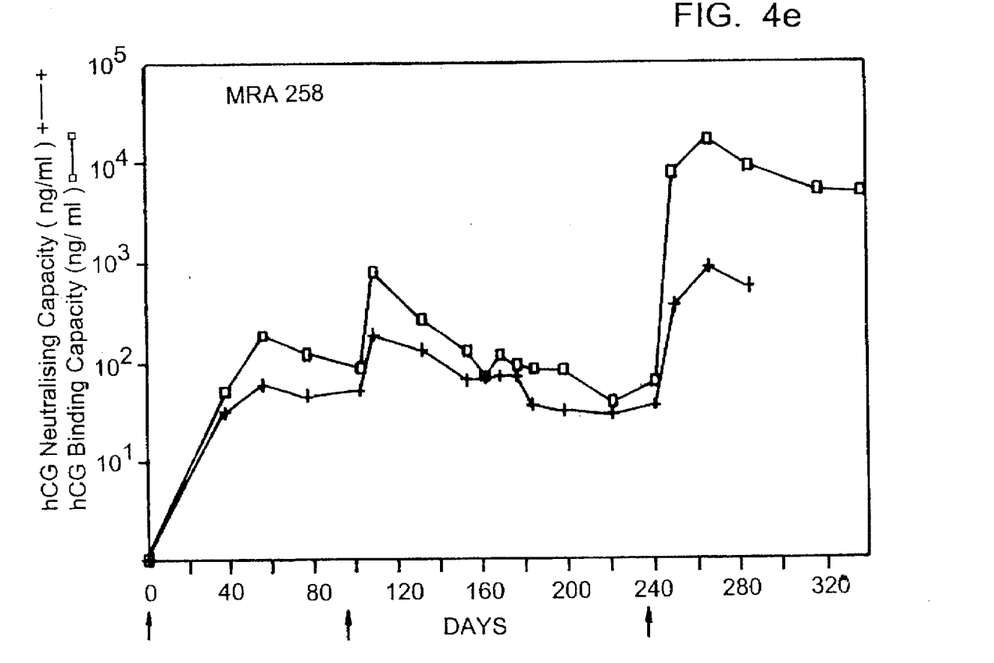
Figure 4F:
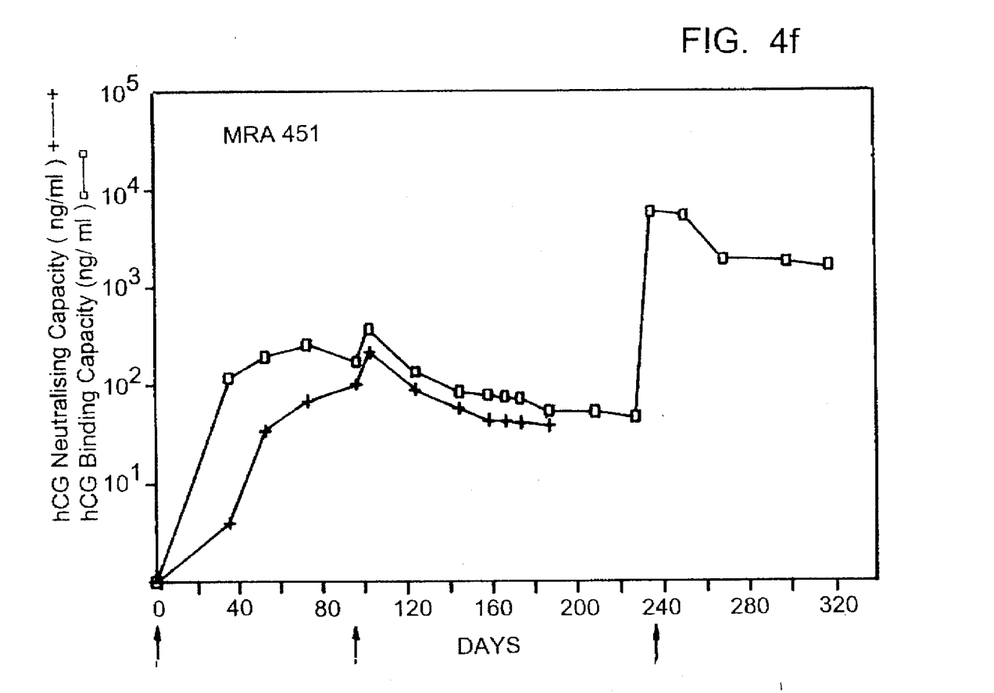
Figure 4G:
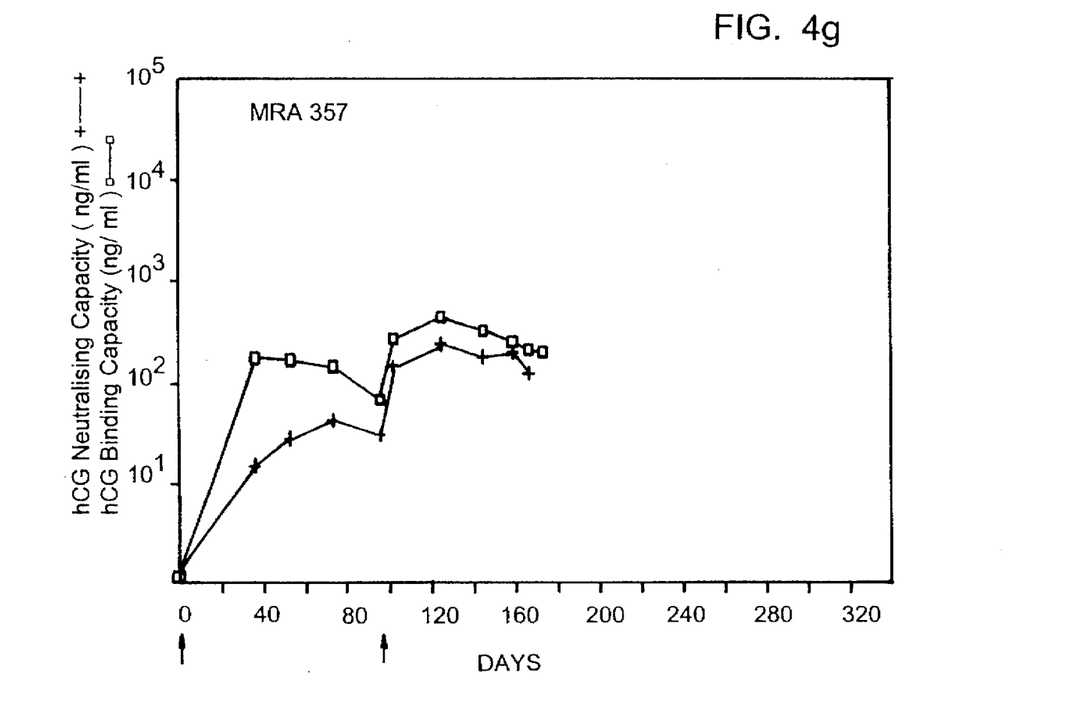
Figure 4H:
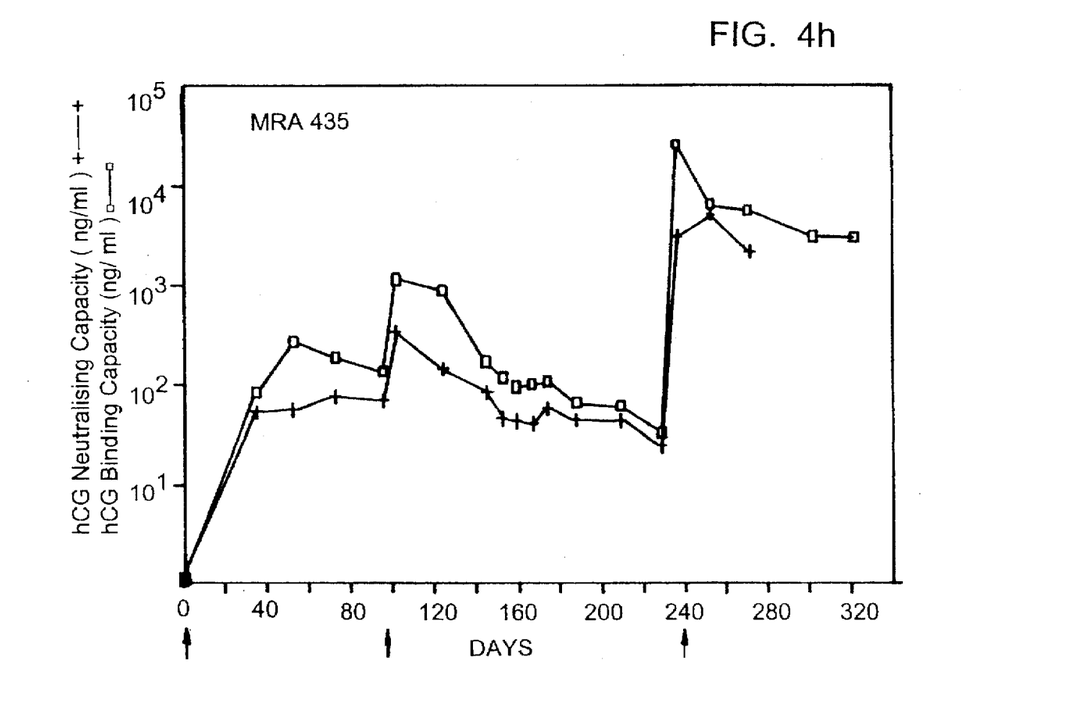
Figure 5:
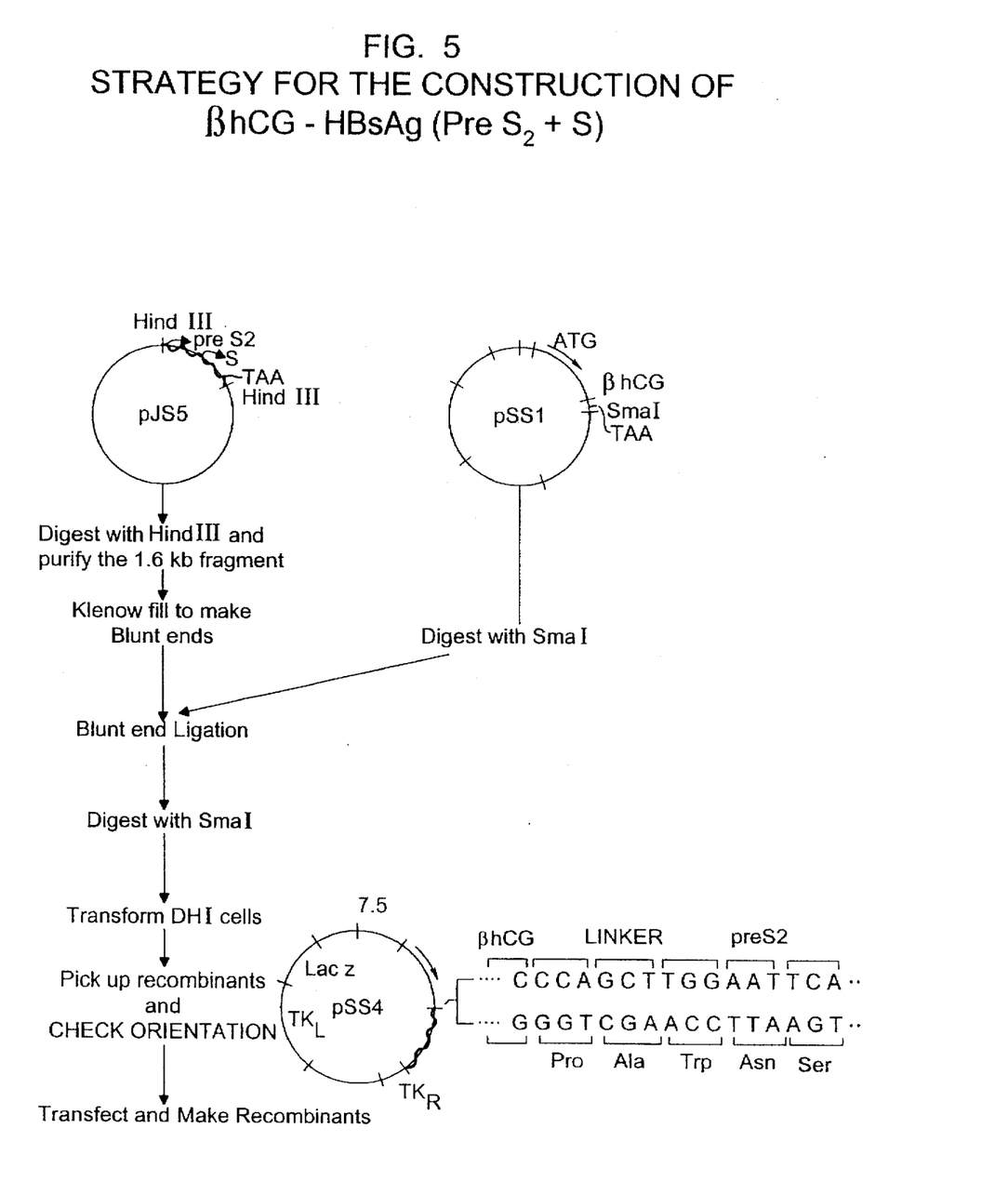
Figure 6:
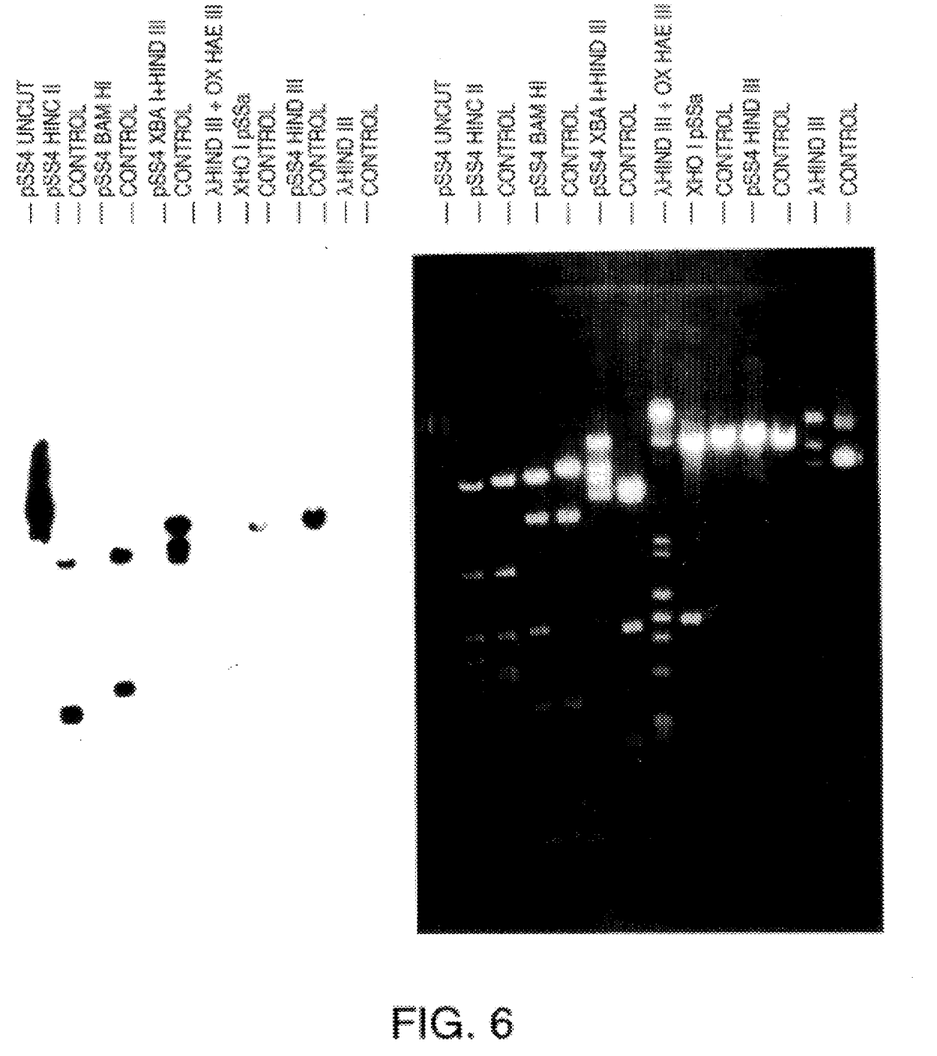
Figure 7:
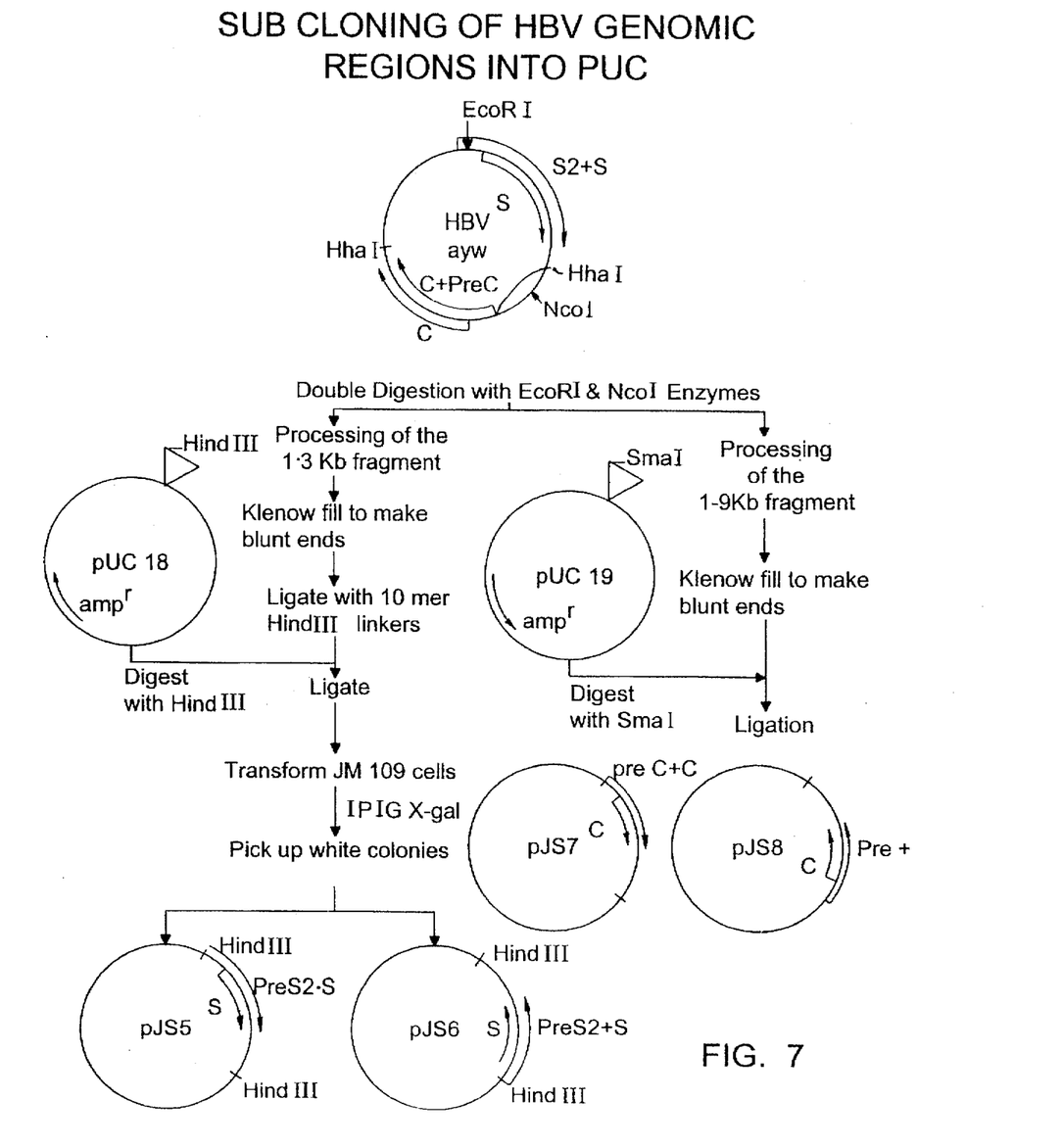

Cloning of BhCG-HBsAq into Vaccinia,

The vector pSSI (see above and FIG. 1), containing beta hCG cDNA in a vaccinia vector, was digested with the restriction endonuclease, Sma I, which cuts just upstream of the BhCG termination codon. The Hind III fragment coding for the entire middle protein of hepatitis B surface protein (pre S +S region) was digested out from the intermediate vector pJS5 (described below), klenow filled and ligated to the Sma I cut pSS1 to give rise to the plasmid pSS4. (FIG. 5). The orientation of the hepatitis B surface protein gene in relation to beta hCG was verified by various restriction enzyme digestions and Southern blotting (FIG. 6). This plasmid was used to make the recombinant vaccinia virus and the recombinants (vSS4) were picked up as described earlier. Cloning of the Intermediate Vector pJS5 :

Hepatitis B genome was cut out of the plasmid pCF80 by EcoRI digestion. The 3.2 kb EcoRI fragment was purified from an agarose gel and was further digested with Nco I to give rise to a fragment of approximately 1.9 kb (coding for X and C proteins) and a fragment of approximately 1.3 kb, (coding for pre S2+S protein of hepatitis B.) 10 mer Hind III linkers were ligated to the 1.3 kb fragment and cloned into the Hind III site of the plasmid pUC 18 to give rise to the plasmids pJS5 & pJS6. The 1.3 kb EcoRI-NcoI fragment was blunt ended and cloned into the Sma I site of the plasmid pUC 19 to give rise to the plasmids pJS7 pJS8 (FIG. 7).

Figure 8:
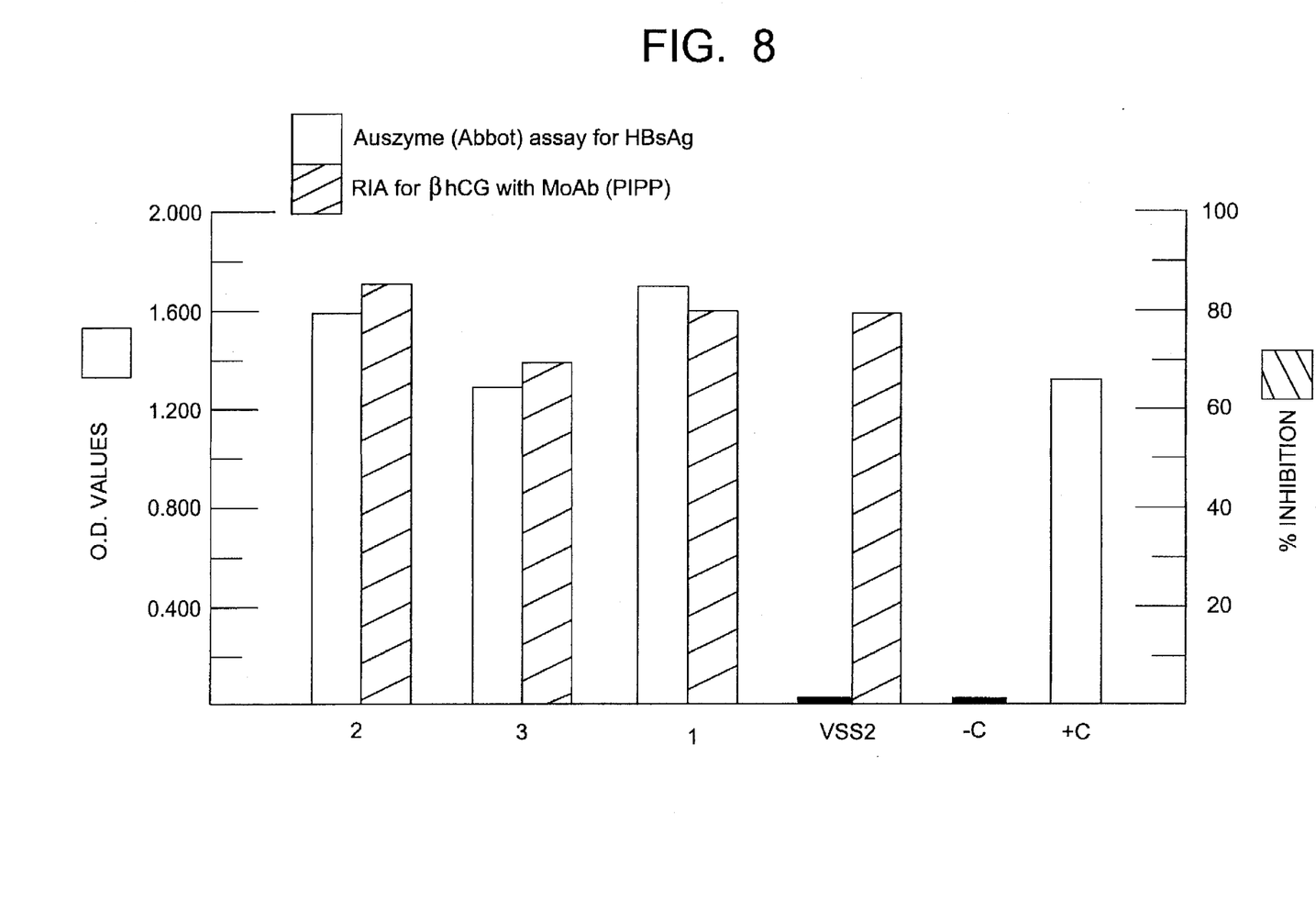

Assay for beta hCG HBsAq:

This recombinant virus (vSS4) expresses both beta hCG, as detected in a competitive radio-immunoassay, as well the surface antigen (HBsAg) as measured bY Abbott's monoclonal antibody based Elisa (FIG. 8).

Figure 9:
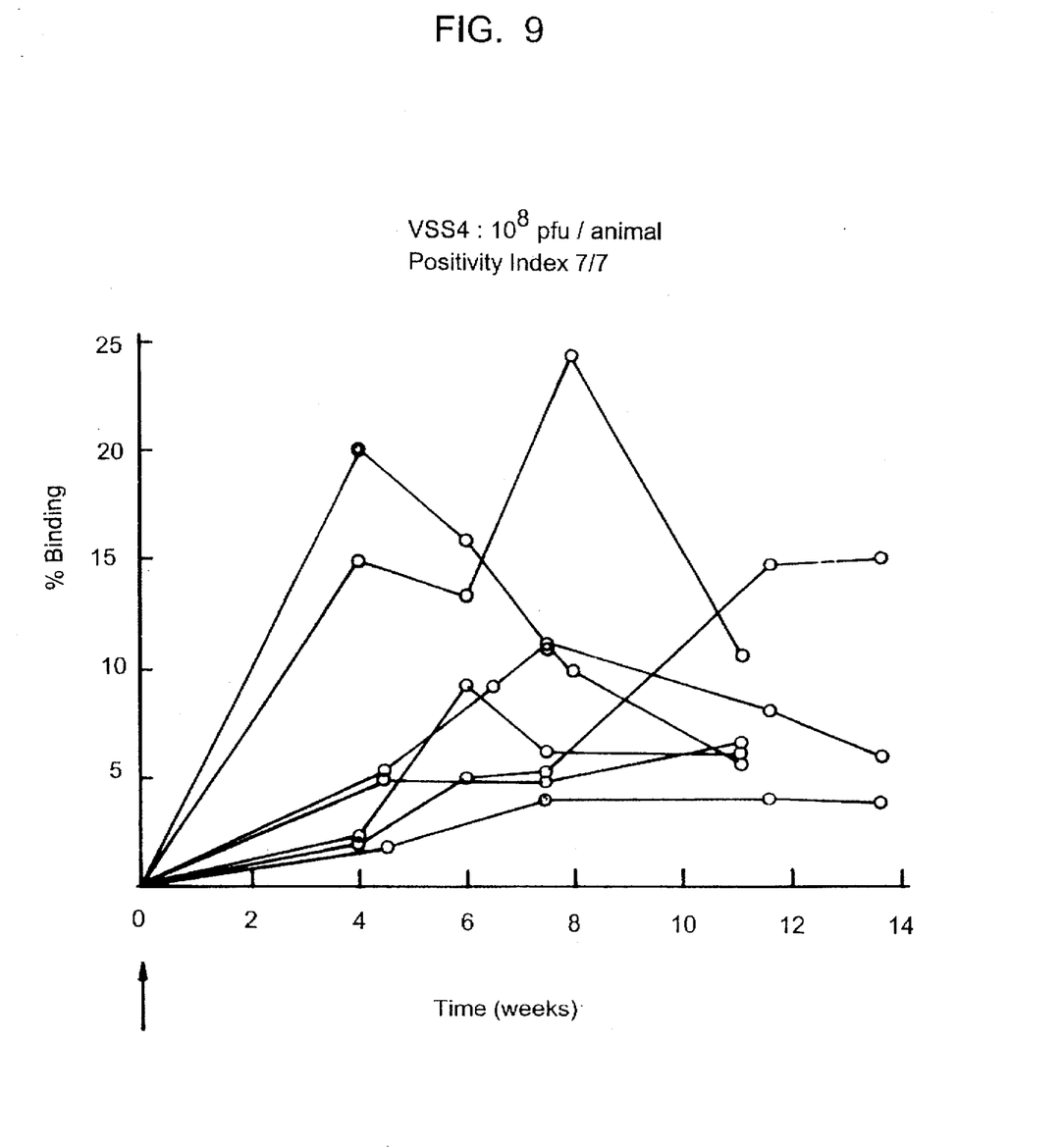

Immunogenicity of Beta hCG-HBsAg Constructs in Vaccinia:

Rats immunized with the above construct by intra-dermal route developed antibodies against hCG (FIG. 9). Being given that antibodies against hCG have been demonstrated to be protective against pregnancy, this version of the vaccine is also usable for control of fertility in women. Furthermore in view of the fact that the gene of Hepatitis B surface protein is also present in the recombinant organism means that the vaccine has immunoprophylactic benefit in a recipient against hepatitis.

The new live recombinant vaccines described here were well tolerated, no side effects were observed during standard acute and subacute toxicology studies in the two animal species studied to date. These vaccines can be employed with conventional pharmaceutically acceptable diluents.

REFERENCES NOT DETAILED IN THE DISCLOSURE

S. Chakrabarti, Srinivasan. J, L. Lall, L. V. Rao and G. P. Talwar: Expression of biologically active human chorionic gonadotropin and its subunits by recombinant vaccinia virus. Gene, 77, (1989) 87–93.

Chakrabarti S, Brechling K and Moss B.: Vaccinia virus expression vector: Co-expression of B-galactosidase provides visual screening of recombinant viral plagues. Mol. Cell. Biol., 5, (1985) 3403–3409.

Jain S. K, Chin W. W and Talwar. G. P.: Isolation and characterization of cDNA clones for and B subunits of ovine luteinizing hormone. J. Biosci., 12, (1987) 349–357.

Lavanya Lall, J. Srinivasan, L. V. Rao, S. K. Jain, G. P. Talwar and S. Chakrabarti.: Recombinant vaccinia virus expresses immunoreactive alpha subunit of Ovine Luteinizing Hormone which associates with B-hCG to generate bioactive dimer. Indian J. Biochem. Biophy., 25, (1988) 510–514.

Talwar G. P, Om Singh and Rao L. V.: An improved immunogen for anti-hCG vaccine eliciting antibodies reactive with conformation native to the hormone without cross-reaction with hFSH and hTSH. J. Repro. Immu., 13, (1988) 53–63.

Om Singh, N. C. Sharma, L. V, Rao, A. Alam A. Gaur and G. P. Talwar (1989): Antibody response and characteristics of antibodies in women immunized with three contraceptive vaccines inducing antibodies against human chorionic gonadotropin. Fertility and St rility: vol. 52, No. 5, 739–744.

We claim:

1. A nucleotide sequence (I) coding for a fused peptide, the sequence consisting of:
   (A) a beta subunit of a mammalian gonadotropin in reading frame alignment with and followed by
   (B) the trans-membrane and cytoplasmic domains of the gene coding for Vesicular Stomatitis Virus Glycoprotein whereby when the nucleotide sequence is inserted into a virus and the virus is used to infect a host cell, the fused peptide is expressed and anchored to the host cell membrane.

2. A nucleotide sequence (I) according to claim 1 which further includes a nucleotide sequence (II) coding for an alpha subunit of ovine luteinizing hormone inserted into a virus, whereby the alpha subunit is capable of binding to the fused peptide on co-expression with the fused peptide in the same host cell.

3. A recombinant vaccinia virus consisting of a nucleotide sequence according to claim 1 inserted into a region of the vaccinia virus genome non-essential for survival of vaccinia virus in a host cell.

4. A recombinant vaccinia virus consisting of a nucleotide sequence according to claim 2 inserted into a region of the vaccinia virus genome non-essential for survival of vaccinia virus in a host cell.

5. A birth control vaccine comprising at least one recombinant virus according to claim 3.

6. A birth control vaccine comprising at least one recombinant virus according to claim 4.

7. A method for controlling fertility in a mammal which comprises administering an effective amount of a birth control vaccine according to claim 5.

8. A method for controlling fertility in a mammal which comprises administering an effective amount of a birth control vaccine according to claim 6.

* * * * *